US008961936B2

(12) United States Patent
Wiley et al.

(10) Patent No.: US 8,961,936 B2
(45) Date of Patent: *Feb. 24, 2015

(54) ULTRASONOGRAPHY USING TIME- AND TEMPERATURE-SENSITIVE VARIABLE ADHESION COUPLING GELS

(75) Inventors: Christopher Wiley, Hanover, NH (US); John A. Merhige, Sudbury, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/241,025

(22) Filed: Sep. 22, 2011

(65) Prior Publication Data

US 2012/0016236 A1  Jan. 19, 2012

Related U.S. Application Data

(63) Continuation of application No. 12/110,721, filed on Apr. 28, 2008, now Pat. No. 8,043,604.

(60) Provisional application No. 60/914,475, filed on Apr. 27, 2007.

(51) Int. Cl.
  *A61K 49/22*   (2006.01)
  *A61K 9/14*    (2006.01)
  *A61B 8/00*    (2006.01)
  *C08L 71/02*   (2006.01)

(52) U.S. Cl.
  CPC .............. *A61B 8/4281* (2013.01); *A61K 49/226* (2013.01); *C08G 2650/58* (2013.01); *C08L 71/02* (2013.01)
  USPC ............................ 424/9.5; 424/486; 424/497

(58) Field of Classification Search
  USPC ............ 424/9.5, 78.1, 484, 486; 600/36, 437, 600/446, 459; 623/1, 11–13
  See application file for complete search history.

(56) References Cited

U.S. PATENT DOCUMENTS

| | | | |
|---|---|---|---|
| 4,002,221 A * | 1/1977 | Buchalter | 181/0.5 |
| 4,365,516 A * | 12/1982 | Molina | 73/644 |
| 4,920,966 A | 5/1990 | Hon et al. | |
| 5,070,888 A | 12/1991 | Hon et al. | |
| 5,394,877 A | 3/1995 | Orr et al. | |
| 5,522,878 A | 6/1996 | Montecalvo et al. | |
| 5,575,815 A | 11/1996 | Slepian et al. | |
| 5,861,174 A | 1/1999 | Stratton et al. | |
| 5,879,662 A | 3/1999 | Gieselmann | |
| 6,048,323 A | 4/2000 | Hon | |
| 6,719,699 B2 | 4/2004 | Smith | |
| 6,866,630 B2 | 3/2005 | Larson et al. | |
| 8,043,604 B2 | 10/2011 | Wiley et al. | |
| 2001/0033825 A1* | 10/2001 | Douglas | 424/9.5 |
| 2003/0149359 A1* | 8/2003 | Smith | 600/437 |

FOREIGN PATENT DOCUMENTS

| | | |
|---|---|---|
| DE | 44 24 233 C1 | 12/1995 |
| EP | 0551626 * | 12/1992 |
| JP | 01-304109 A | 12/1989 |
| JP | 11-318898 A | 11/1999 |
| JP | 2007-143946 A | 6/2007 |
| KR | 10-2001-0088066 A | 9/2001 |
| WO | WO 97/30736 A2 | 8/1997 |
| WO | WO 03/094710 A2 | 11/2003 |

OTHER PUBLICATIONS

F.Tirnksiz et al., Rheological, mucoadhesive and releae properties of Pluronic F-127 gel and Pluronic F-127/polycarbophil mixed gel systems, Pharmazie, 60, 7, 2005.*
American College of Emergency Physicians, *Use of Ultrasound Imaging by Emergency Physicians*, Annals of Emergency Medicine 469-470 (2001).
Cabana et al., *Study of the Gelation Process of Polyethylene Oxide$_a$-polypropylene oxide$_b$-Polyethylene Oxide$_a$ Copolymer (Polyxamer 407) Aqueous Solutions*, 190 Journal of Colliod and Interface Science 307-312 (1997).
March et al., *Pharmacokinetics of Adenoviral Vector-Mediated Gene Delivery to Vascular Smooth Muscle Cells: Modulation by Poloxamer 407 and Implications for Cardiovascular Gene Therapy*, 6 Human Gene Therapy 41-53 (Jan. 1995).
International Search Report issued on Sep. 11, 2008 by the Korean Patent Office in corresponding International Patent Application No. PCT/US2008/061769.
O'Brien, J.M., et al., "Methylcellulose Gel Is a Superior Contrast Agent for Ultrsound Exmaination of the Cervix in Obstetric Patients", Ultrasound Obstet Gyneco1,21: 149-151 (2003).
International Report on Patentability for PCT/US2008/061769, "Ultrasounography Using Time-and Temeprature-Sensitive Variable Adhesion Coupling Gels", date of mailing Oct. 27, 2009.
Extended Search Report for EP 08747023.3, "Ultrasounography Using Time-and Temeprature-Sensitive Variable Adhesion Coupling Gels", date of mailing Aug. 21, 2014.

* cited by examiner

*Primary Examiner* — Michael G Hartley
*Assistant Examiner* — Jagadishwar Samala
(74) *Attorney, Agent, or Firm* — Hamilton, Brook, Smith & Reynolds, P.C.

(57) ABSTRACT

One aspect of the present invention relates to a method of ultrasonography, utilizing a gel comprising a reverse phase polymer which facilitates the transmission of high-frequency sound waves. Further, the inherent properties of the reverse phase polymer result in increased adhesion at higher temperatures, thereby helping to maintain the desired position of the ultrasound probe until the user intends to adjust the probe's position. In certain embodiments, the method is utilized in a medical procedure in which stability of an ultrasound probe or transducer in an intended desired position can improve the outcome or increase the efficiency of the procedure. In certain embodiments, the gel further comprises an additive to increase the ultimate adhesion of the gel. In still other embodiments, the gel can be used on the skin, on a protective sheath encasing an ultrasound probe, or between the sheath and the probe, or any or all of them.

14 Claims, 12 Drawing Sheets

Philips HD11XE
8 MHz

A            B

Philips HD11XE
10 MHz

Sonosite MicroMAXX
"Gen"

A  B

Sonosite MicroMAXX
"Pen"

Zonare
"10 MHz"

A　　　　　　　　　B

Zonare
"17 MHz"

A　　　　　　　　　B

ULTRASONOGRAPHY USING TIME- AND TEMPERATURE-SENSITIVE VARIABLE ADHESION COUPLING GELS

RELATED APPLICATIONS

The present application is a continuation of, and claims priority pursuant to 35 U.S.C. §120 to U.S. patent application Ser. No. 12/110,721 filed Apr. 28, 2008, which claims priority pursuant to 35 U.S.C. §119 to U.S. Provisional Patent Application No. 60/914,475, filed Apr. 27, 2007. The entire contents of each of these applications are hereby incorporated by reference in this application.

FIELD OF THE INVENTION

The invention relates to the field of coupling gels used to aid in the transmission of ultrasound waves, and to the use of ultrasound probe position fixation devices.

BACKGROUND OF THE INVENTION

Ultrasonography

Ultrasonography, also known as sonography, is a technique used in medical imaging in which high-frequency sound waves (typically between 1 and 20 MHz) are reflected off internal organs and the echo pattern is converted into a picture of the structures beneath the transducer. Because ultrasound images are captured in real-time, they can show the structure and movement of the body's internal organs, as well as blood flowing through blood vessels.

Ultrasound examinations can help to diagnose a variety of conditions and to assess organ damage following illness. Ultrasound is used to help physicians diagnose symptoms such as pain, swelling and infection. Ultrasound is a useful way of examining many of the body's internal organs and conditions, including but not limited to the: heart and blood vessels, including the abdominal aorta and its major branches (for example, for abdominal aortic aneurism); liver; gallbladder; spleen; pancreas; kidneys; bladder; uterus, ovaries, and unborn child (fetus) in pregnant patients; ectopic pregnancy; eyes; thyroid and parathyroid glands; scrotum (testicles); and breast. Ultrasound is also used to diagnose a variety of heart conditions and to assess damage after a heart attack or other illness.

In addition, ultrasound is increasingly used to guide medical procedures such as those involving needle puncture. Examples include, but are not limited to; needle delivery of anesthesia; placement of central venous catheters; placement of pulmonary artery catheters; needle biopsy and fine needle aspiration; amniocentesis; femoral catheter placement; and, egg harvesting. In these and other applications, a sterile coupling gel is often used. The ultrasound transducing surface is coated with a sterile or non-sterile gel, and then the transducer may be placed in a sterile fragile sheath. The outer surface of the sheath, or the surface of the patient's skin, is then coated with sterile ultrasound gel.

Conventional methods for targeted delivery of local anesthesia have been utilized with varying success for decades. A traditional method includes assessing needle location using the tactile feedback (clicks, pops) that the needle generates as it penetrates tissue adjacent to the desired nerve site. Another method attempts to correctly locate the anesthesia needle using paresthesia, the abnormal neurological sensations that results when the needle touches the intended nerve.

A slightly more advanced method to guide anesthesia delivery which has largely supplanted the older methods of clicks, pops or paresthesia is that of nerve stimulation. In this method, an insulated needle is attached to an electrically charged live wire. As the needle approaches the nerve, the patient will experience an involuntary movement caused by the electrically charged needle stimulating the desired nerve once it is sufficiently close to the nerve.

In addition to being unreliable in correctly identifying the nerve, these conventional procedures are fairly slow and can be unsafe to the patient due to the need for multiple and/or incorrectly placed injections. Ultrasound guided delivery of anesthesia provides a more effective, safer and faster alternative to these conventional approaches.

Central venous catheter line placement has also been traditionally executed using a 'feel' approach. Certain anatomical landmarks such as bones are used to identify the location of the jugular vein. However, obesity, vascular disease, hypotension, and many other factors can create a unique set of challenges in correctly identifying the location for even the most experienced healthcare provider. The American College of Emergency Physicians has recognized the importance of this skill by including it in the 2001 policy statement "Use of Ultrasound Imaging by Emergency Physicians" (Ann. Emerg. Med. 2001; 38:469-70), which calls ultrasound-guided central venous access one of the "primary applications for emergency ultrasound."

In performing needle biopsy, such as breast biopsy, ultrasound guidance has proven quite valuable. After placing an ultrasound probe over the site of the breast lump and using local anesthesia, the radiologist guides a biopsy needle directly into the mass. Tissue specimens are then taken using either an automatic spring-loaded or vacuum-assisted device (VAD). Ultrasound is most often used to guide breast biopsy when a breast abnormality is visible on ultrasound. When it is necessary to do an open surgical biopsy, a guide wire first is passed directly into the mass. This procedure also may be guided by ultrasound.

Other broad applications of sonography include phonophoresis and wound healing. Phonophoresis (also known as sonophoresis or ultrasonophoresis) is the movement of a medication or other substance through the skin by the application of sonic radiation to the medicament placed upon the skin. In wound healing, ultrasound plays a role because it has been well established that ultrasound by itself can speed up the healing process in open wounds.

More recently, the use of high intensity focused ultrasound (HIFU) for therapeutic purposes, as opposed to imaging, has received significant attention in the medical community. HIFU therapy employs ultrasound transducers that are capable of delivering 1,000-10,000 W/cm$^2$ to a focal spot, in contrast to diagnostic imaging ultrasound, where intensity levels are usually below 0.1 W/cm$^2$. A portion of the energy from these high intensity sound waves is transferred to the targeted location as thermal energy. The amount of thermal energy thus transferred can be sufficiently intense to cauterize undesired tissue, or to cause necrosis of undesired tissue (by inducing a temperature rise to beyond 70° C.) without actual physical charring of the tissue. Tissue necrosis can also be achieved by mechanical action alone (i.e., by cavitation that results in mechanical disruption of the tissue structure). Further, where the vascular system supplying blood to an internal structure is targeted, HIFU can be used to induce hemostasis. The focal region of this energy transfer can be tightly controlled so as to obtain necrosis of abnormal or undesired tissue in a small target area without damaging adjoining normal tissue. Thus, deep-seated tumors can be destroyed with HIFU without surgical exposure of the tumor site.

Ultrasound Coupling Gels

Sound waves are poorly transmitted by air and thus require a coupling mechanism for proper transmission. This coupling mechanism is commonly a viscous fluid or gel which, due to its physical and acoustic properties, acts to displace air, fill contours between the piezoelectric transducer and the body, and enable successful transfer of the acoustic energy. Many ultrasound coupling gels exist in the market place in both sterile and non-sterile forms. Sterile ultrasound gels include Sterile Aquasonic® 100 (Parker Labs, Inc., Orange, N.J., 07050), Ultra/Phonic™ (Pharmaceutical Innovations, Newark, N.J.), UltraBio Sterile (Sonotech, Bellingham, Wash., 98225) and Sonogel—Sterile (Sonogel Vertriebs GmbH, D-65520 Bad Camberg). Sterile ultrasound gels are typically provided in single-use individually wrapped sterile foil pouches of 20 g each. The UltraBio product (U.S. Pat. No. 6,866,630 to Larson et al.) describes an in vivo biocompatible, bioeliminating sterile diagnostic ultrasound imaging couplant and lubricant.

Some ultrasound applications, for example fetal ultrasound, desire the ability to continuously move and reposition the ultrasound probe in order to gain multiple images at multiple angles of multiple sites. Other ultrasound applications, such as but not limited to the ultrasound guided procedures described above, desire the ability to move the ultrasound transducer until an optimal position is located, and then desire the probe to remain stable in this position until the user intentionally adjusts the position of the probe. In these applications, the ultrasound probe is commonly held in one hand of the caregiver while the procedure requiring guidance is performed with the other hand. Current ultrasound coupling gels generally exhibit a slippery or low friction state and thus leave the probe susceptible to unwanted movement, potentially leading to loss of visualization of the target site, the need to relocate the site, misguided or repeat punctures and an overall decrease in safety, effectiveness and procedure efficiency.

Efforts to utilize adhesive or bioadhesive coupling agents have been disclosed. U.S. Pat. No. 5,522,878 to Montecalvo et al. describes a solid, multipurpose, flexible, ultrasonic, biomedical couplant hydrogel in sheet form to facilitate transfer of ultrasound energy to and from a patient. Also described is a method of attaching the sheet to skin to hold the couplant gel in place during an exam, which constitutes a band of pressure sensitive adhesive bonded to plastic foam, such as foamed rubber, that is located along the outer perimeter of the sheet. The hydrogel sheet described is not adhesive in and of itself, but depends on sufficient perspiration to make the gel somewhat tacky. The adhesive border, so described, is not acoustic self-coupling, therefore restricting ultrasound scanning to areas exclusive of those covered with adhesive covered foam. The level of adhesion of the hydrogel sheet is fixed and the tacky surface is only between the skin and the sheet. It is meant to cling to the skin while the transducer moves freely on top of it. It is not intended to aid in the maintenance of the probe's final position, but rather to improve ease of handling by being easily applied to and removed from the body.

U.S. Pat. No. 6,719,699 to Smith describes adhesive hydrogel films or sheets as acoustic coupling media attachable to the active face (transducer) of ultrasound instruments (such as probes or scanheads) and to the inner face of latex, polyurethane or other polymeric probe covers; thereby, enabling the transfer of acoustic energy between an ultrasound probe and an object of interest when used in conjunction with a gel or liquid ultrasound couplant on the skin surface. The adhesive hydrogel comprises acoustic transmission media and is adhesive on both sides of the film. Such adhesive hydrogels films are so comprised as to render desirable levels of acoustic transmission with acceptable low levels of acoustic artifacts, distortion and attenuation. The invention of U.S. Pat. No. 6,719,699 allows for an adhesion between the probe surface and the inner face of a probe cover. The invention does not aid in the effort of helping to secure or fix the probe in an intended desired position. Nor does the invention describe a gel which varies in adhesion and viscosity over time.

U.S. Pat. No. 5,394,877 to Orr et al. describes a contact medium structure attachable to externally applied medical diagnostic devices for providing self-adherence of a medical device to the skin of a patient thereby eliminating the need for retaining belts or similar means. A contact medium is described that is inherently adhesive, hydrophilic, skin compatible, ultrasonic compatible and pressure sensitive to facilitate self-adhesion of the medical device to the patient's skin. The device of Orr et al. necessitates the use of a flexible support element which must be manually set in place to fix the ultrasound probe in its desired position. The inherently adhesive contact medium has a fixed adhesion. It does not allow for easy positioning of the transducer followed by a natural and automatic inherent increase in adhesion and viscosity to assist in holding the transducer in the desired position. Because the invention utilizes the flexible support element which holds a mesh-reinforced hydrogel film in place, it is not conducive to ultrasound guided procedures such as needle guided procedures as previously discussed.

U.S. Pat. No. 5,070,888 to Hon et al. details the use of a strong adhesive on the abdomen of a patient that forms a solid bond with the skin in order to secure the transducer to the patient. U.S. Pat. No. 4,920,966 to Hon et al. describes an adhesive layer applied to the surface of a disc-shaped transducer base in contact with the skin. Such an adhesive in these patents is sufficiently strong to maintain the transducer in place on the patient without the use of a belt. However, such a system is difficult to remove because the adhesive would bond to the skin of the patient and require the use of solvents for the removal of the transducer from the patient. The inherently adhesive contact medium has a fixed adhesion. It does not allow for easy positioning of the transducer followed by a natural and automatic inherent increase in adhesion and viscosity to assist in holding the transducer in the desired position.

U.S. Pat. No. 6,048,323 to Hon et al. describes the use of a hydrogel layer present on the lower surface of a fastening pads for attachment to the patient. The hydrogel is a mild adhesive which is sufficiently strong to provide the necessary fixation forces to fix the transducer support plate on the patient, but does not form a strong bond with the skin of the patient. The hydrogel is easily removed from the skin of the patient without the use of solvents. This hydrogel requires the use of an additional fastening pad, and does not experience the increase in adhesion over time that first allows positioning before aiding in anchoring the transducer in the desired position. It is also not suitable for guided injection procedures due to the use of the fastening pad.

In light of the aforementioned problems with current techniques, it would be advantageous to have an ultrasound coupling gel which initially allows for easy movement and positioning of the ultrasound transducer, and then inherently increases in viscosity and adhesion over time, assisting in fixing the probe to the skin in the desired position, all the while providing for consistent contact with the patient's skin to allow for proper transmission of the wave signal. Additionally, it would be advantageous to have the aforementioned product which allows for unimpeded ultrasound guided procedures such as needle injection, and the ability to intentionally remove or reposition the transducer if desired even after ultimate adhesion has been achieved.

SUMMARY OF THE INVENTION

The present invention relates to a variable adhesion ultrasound coupling gel. A reverse phase acoustic coupling gel initially allows easy movement and positioning of the ultrasound transducer before experiencing an inherent marked increase in viscosity and adhesion which assists in fixing the probe in place once the desired position is identified. Once ultimate adhesion is achieved, the gel will continue to allow intentional repositioning or removal of the transducer. The coupling gel allows for unimpeded ultrasound guided procedures such as ultrasound guided needle puncture. By first allowing the healthcare provider to easily position the ultrasound transducer, and then assisting in the fixation of the transducer in the desired position, the coupling gel enables a more effective, safer and shorter procedure in ultrasound guided procedures.

DESCRIPTION OF THE INVENTION

The device of this invention is a time- and temperature-sensitive variable adhesion ultrasound coupling gel. A reverse phase polymer is utilized as an ultrasound acoustic coupling gel. The coupling gel is initially in a low viscosity, low adhesion state when applied to the surface of the patient's skin, allowing the ultrasound transducer to be easily moved and positioned while identifying the desired location. The gel experiences an inherent increase in adhesion and viscosity when exposed to the skin for a period of time, providing a non-permanent adhesion to the surface of the skin and assisting in fixing the transducer in its intended location. The gel also experiences varying viscosity in response to varying shears applied to the gel. As the shear applied decreases, the viscosity of the gel increases, while increasing shear yields decreasing viscosity. This feature of the gel allows for intentional repositioning or removal of the ultrasound transducer after ultimate adhesion has been reached. The gel is easily cleaned from the skin without the use of solvents when the procedure is complete. The coupling gel also allows for unimpeded ultrasound guided procedures. By first allowing the healthcare provider to easily position the ultrasound transducer, and then assisting in the fixation of the transducer in the desired position, the coupling gel enables a more effective, safer and shorter procedure in ultrasound guided procedures. The coupling gel is biocompatible and its components are non-irritating.

The reverse phase polymer can include a poloxamer. The term "poloxamer" denotes a symmetrical block copolymer, consisting of a core of PPG polyoxyethylated to both its terminal hydroxyl groups, i.e. conforming to the interchangeable generic formula (PEG)X-(PPG)Y-(PEG)X and (PEO)X-(PPO)Y-(PEO)X. Each poloxamer name ends with an arbitrary code number, which is related to the average numerical values of the respective monomer units denoted by X and Y.

The term "reverse phase polymer" as used herein refers to a polymer that is typically encountered as a solution at ambient temperature, but which undergoes a gelation at or near physiological temperature. Reverse phase polymers include poloxamer 407 (BASF Pluronic® F127), poloxamer 188 (BASF Pluronic® F68), poloxamer 288 (BASF Pluronic® F98), poloxamer 338 (BASF Pluronic® F108), poly(N-isopropylacrylamide), poly(methyl vinyl ether), poly(N-vinylcaprolactam); and certain poly(organophosphazenes). See Bull. Korean Chem. Soc. 2002, 23, 549-554.

In general, the reverse phase polymers used in the methods of the invention, which become a viscous gel at or about skin surface temperature, can be dispelled onto the patient's skin in a low viscosity form resembling that of a liquid or free-flowing lower viscosity gel. The dispelled material once approaching skin surface temperature undergoes a transition from a liquid or free-flowing gel to a more viscous gel, thereby also experiencing an increase in adhesion. Additionally, the reverse phase polymer can be a shear-thinning material, in which the viscosity increases as the applied shear decreases, and conversely the viscosity decreases as the applied shear increases. The reverse phase polymers used in connection with the methods of the invention may comprise a block copolymer with reverse thermal gelation properties. The block copolymer can further comprise a polyoxyethylene-polyoxypropylene block copolymer such as a biodegradable, biocompatible copolymer of polyethylene oxide and polypropylene oxide. Also, the reverse phase polymer can include a therapeutic agent such as an antiseptic agent. The reverse phase polymer can also include additives to increase the ultimate adhesion of the gel. The reverse phase polymer can also include viscosity modifiers, such as sodium chloride, to adjust the viscosity of the gel. The reverse phase polymer can also include additives, such as preservatives or antimicrobials, to extend the shelf life of the gel.

Notably, poloxamer polymers (trade name Pluronic® polymers) have unique surfactant abilities and extremely low toxicity and immunogenic responses. These products have low acute oral and dermal toxicity and low potential for causing irritation or sensitization, and the general chronic and sub-chronic toxicity is low. In fact, Pluronic® polymers are among a small number of surfactants that have been approved by the FDA for direct use in medical applications and as food additives (BASF (1990) Pluronic® & Tetronic® Surfactants, BASF Co., Mount Olive, N.J.). Recently, several Pluronic® polymers have been found to enhance the therapeutic effect of drugs, and the gene transfer efficiency mediated by adenovirus. (March K L, Madison J E, Trapnell B C. "Pharmacokinetics of adenoviral vector-mediated gene delivery to vascular smooth muscle cells: modulation by poloxamer 407 and implication for cardiovascular gene therapy" Hum Gene Therapy 1995, 6, 41-53).

The molecular weight of the reverse phase polymer is preferably between about 1,000 and about 50,000, more preferably between about 5,000 and about 35,000. Preferably the polymer is in an aqueous solution. For example, typical aqueous solutions contain about 10% to about 50% polymer, preferably about 20% to about 40%. The molecular weight of a suitable reverse phase polymer (such as a poloxamer) may be, for example, between about 5,000 and about 25,000, and more particularly between about 7,000 and about 20,000.

The pH of the reverse phase polymer formulation is, generally, about 3.0 to about 8.0, more preferably between about 5.0 and about 7.8, which are suitable pH levels for exposure to mammalian skin. The pH level may be adjusted by any suitable acid or base, such as hydrochloric acid or sodium hydroxide.

Suitable reverse phase polymers include polyoxyethylene-polyoxypropylene (PEO-PPO) block copolymers. Three examples are Pluronic® F127, F98, and F108, which are PEO-PPO block copolymers with molecular weights in the range of about 12,600 to about 14,600. Each of these compounds is available from BASF of Mount Olive, N.J. Pluronic® F98 at about 12-45% concentration in saline tromethamine solution in purified water (Tris) is an example of a suitable reverse phase polymeric material. Pluronic® F108 at about 12-45% concentration in Tris is another example of a suitable material. Pluronic® F127 at about 12-45% concentration in Tris is another example of a suitable material. Low concentrations of dye (such as crystal violet), hormones, therapeutic agents, fillers, antiseptics and antibiotics can be added to the reverse phase polymer. In general, other biocompatible, biodegradable PEO-PPO block copolymers that exist as a gel at skin surface temperature and as a liquid or low viscosity gel at below skin surface temperature may also be used according to the present invention.

The average molecular weights of the poloxamers range from about 1,000 to greater than 16,000 daltons. Because the poloxamers are products of a sequential series of reactions, the molecular weights of the individual poloxamer molecules form a statistical distribution about the average molecular weight. In addition, commercially available poloxamers contain substantial amounts of poly(oxyethylene) homopolymer and poly(oxyethylene)/poly(oxypropylene) diblock polymers. The relative amounts of these byproducts increase as the molecular weights of the component blocks of the poloxamer increase. Depending upon the manufacturer, these byproducts may constitute from about 15 to about 50% of the total mass of the polymer.

The reverse phase polymers may be purified using a process for the fractionation of water-soluble polymers, comprising the steps of dissolving a known amount of the polymer in water, adding a soluble extraction salt to the polymer solution, maintaining the solution at a constant optimal temperature for a period of time adequate for two distinct phases to appear, and separating physically the phases. Additionally, the phase containing the polymer fraction of the preferred molecular weight may be diluted to the original volume with water, extraction salt may be added to achieve the original concentration, and the separation process repeated as needed until a polymer having a narrower molecular weight distribution than the starting material and optimal physical characteristics can be recovered.

Additives to increase the ultimate adhesion of the gel can include suitable high molecular weight polyacrylic acid polymers such as Carbopols® from The Lubrizol Corporation (formerly Noveon, Inc., Cleveland, Ohio). Suitable Carbopols® include Carbopol® 981 NF, Carbopol® 980NF, Carbopol® 971 NF, Carbopol® 974NF, Carbopol® 941 NF, Carbopol® 940NF. Carbopol® 981 NF is commonly used for topical applications. The average viscosity of the Carbopols® ranges from about 4,000 to about 65,000 cP, and preferably between about 4,000 and about 30,000 cP, at about 0.5% wt concentration and about 7.5 pH.

The preferred embodiment of the ultrasound coupling gel includes poloxamer 288 and Carbopol® 981 NF in a solution of purified water or tromethamine in purified water (Tris). The concentration of poloxamer 288 ranges from about 10% (w/w) to about 50% with the preferred range between about 20% and about 40%. The concentration of Carbopol® 981 NF ranges from about 0.1% to about 3% with the preferred range between about 0.5% and about 2% (wt/wt). The balance of the solution is purified water, tromethamine in purified water, or a buffer solution.

Other embodiments of the reverse phase polymer include poloxamer 407 (Pluronic® F127), poloxamer 188 (Pluronic® F68), poloxamer 288 (Pluronic® F98), poloxamer 338 (Pluronic® F108), poly(N-isopropylacrylamide), poly(methyl vinyl ether), poly(N-vinylcaprolactam), certain poly(organophosphazenes), and other reverse phase polymers. These other embodiments can include adhesion additives such as Carbopol® 981 NF, Carbopol® 980NF, Carbopol® 971NF, Carbopol® 974NF, Carbopol® 941NF, and Carbopol® 940NF. The concentration of reverse phase polymer ranges from about 10% (w/w) to about 50% with the preferred range between about 20% and about 40%. The concentration of adhesion additives ranges from about 0.1% to about 3% with the preferred range between about 0.5% and about 2% (wt/wt). The balance of the solution can be purified water, saline solution, phosphate buffered saline solution, or tromethamine in purified water (Tris).

Still other embodiments may include reverse phase polymers that have undergone the purification/fractionation process described above.

Still other embodiments may include any additives to increase ultimate adhesion of the coupling gel, including but not limited to: polycarbophil; sodium alginate; sodium chloride; sodium dihydrogen phosphate; sodium monohydrogen phosphate; protamine; and, polysaccharide.

Still other embodiments may include any additives that would act to modify the viscosity of the reverse phase polymer.

Still other embodiments may include any additives that would not eliminate the reverse phase thermosensitive properties of the gel as described in this invention.

The transition from the low viscosity/low adhesion state to the higher viscosity/higher adhesion state will occur between about 1 and about 180 seconds, and preferably between about 5 and about 90 seconds, In procedures where an ultrasound probe is covered by a protective sheath as previously mentioned, the ultrasound coupling gel of the present invention not only provides acceptable lubricating and/or acoustic coupling properties on the outside of the protective sheath but also within the sheath (i.e. between the ultrasound probe and the sheath).

It is also within the scope of the present invention to apply the inventive couplant directly to an organ or tissue, and then proceed with ultrasound imaging by contacting the couplant-coated organ or tissue with the active area of a transducer. It is to be understood that while the present invention has been discussed with reference to medical ultrasound applications within and on a human body, it is not to be limited thereto. The present invention is also contemplated to be applicable within other animals such as in veterinary ultrasound.

While the invention has been described with reference to preferred embodiments it is to be understood that the invention is not limited to the particulars thereof. The present invention is intended to include process, formulation and modifications which would be apparent to those skilled in the art to which the subject matter pertains without deviating from the spirit and scope of the specification.

EXEMPLIFICATION

The invention now being generally described, it will be more readily understood by reference to the following examples, which are included merely for purposes of illustration of certain aspects and embodiments of the present invention, and are not intended to limit the invention.

EXAMPLE 1

Figure 1:
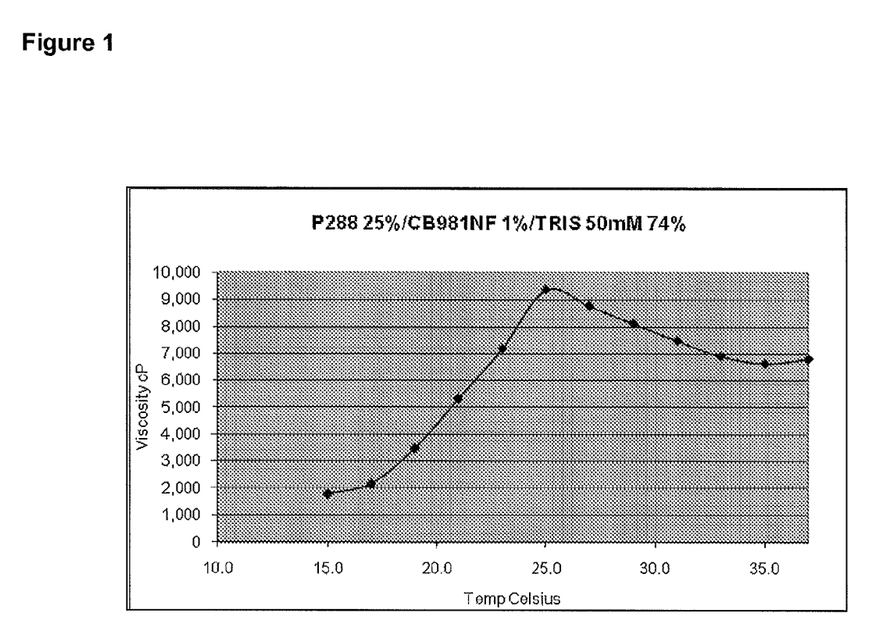
FIG. 1 depicts the dependence of viscosity (cP) on temperature (° C.) of a solution of poloxamer 288 (BASF Pluronic® F98) (25% w/w) and Carbopol 981NF (Lubrizol®) (1% w/w) in a 50 mM tromethamine solution in purified water. The viscosity was recorded using a Brookfield DV-II+ Pro viscometer at 50 rpm.

Poloxamer 288 (BASF Pluronic® F98) and Carbopol 981 NF (Lubrizol®) were added to a solution of tromethamine (50 mM in purified water, pH 7.3) to create a solution of 25% (w/w) P288, 1% Carbopol 981NF, and 74% tromethamine buffer. Viscosity was recorded over a temperature range of 15° C. to 37° C. using a Brookfield DV-II+ Pro viscometer set at 50 rpm. The resulting viscosity vs. temperature curve is presented in FIG. 1. FIG. 1 displays the reverse-thermosensitive nature of the solution due to the inclusion of P288. The peak viscosity of 9,366 cP at 25° C. was 427% that of the viscosity at 15° C. This significant increase in viscosity, along with the increased bioadhesion due to the presence of Carbopol, resulted in a less slippery surface for the ultrasound probe, thus reducing unwanted probe movement. With a peak viscosity encountered above room temperature, the gel was less viscous upon initial application and became more viscous upon warming due to the skin's temperature.

Figure 2:
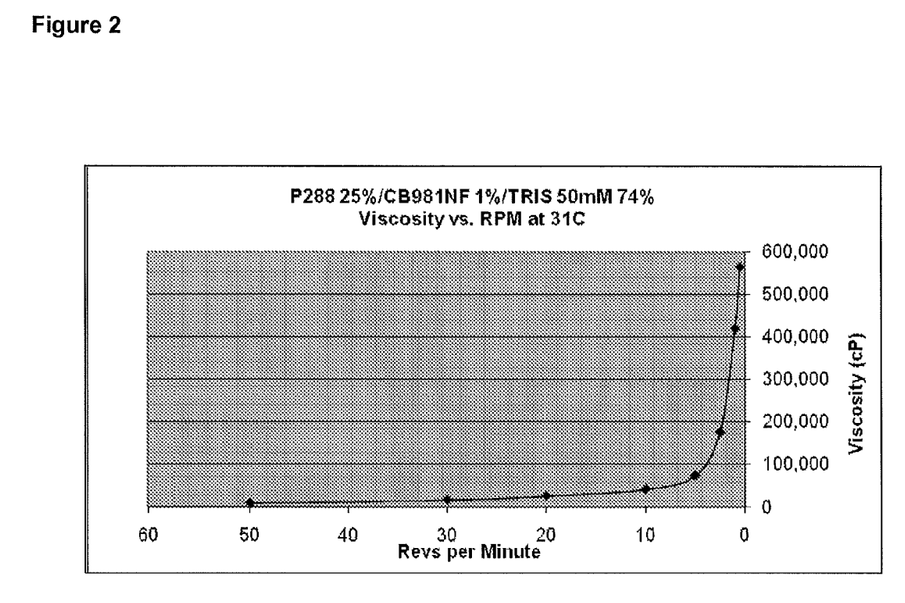
FIG. 2 shows a rheological experiment illustrating the shear thinning nature of a solution of poloxamer 288 (BASF Pluronic® F98) (25% w/w) and Carbopol 981 NF (Lubrizol®) (1% w/w) in a 50 mM tromethamine solution in purified water using the Brookfield viscometer ranging from 50 rpm to 0.5 rpm at 31° C.

Rheology was then performed using the Brookfield viscometer ranging from 50 rpm to 0.5 rpm at 31° C. The data are presented in FIG. 2. FIG. 2 displays the shear thinning nature of the solution. As the shear increased due to increasing rate of rotation of the viscometer, the viscosity decreased. This effect is significant in the ultrasound application. As the probe was brought to rest upon identifying the target location, the lack of shear stress on the gel yielded a more viscous gel. If the user initiated probe movement to fine-tune the probe location, the viscosity of the gel decreased, thus allowing easier movement of the probe.

EXAMPLE 2

Figure 3:
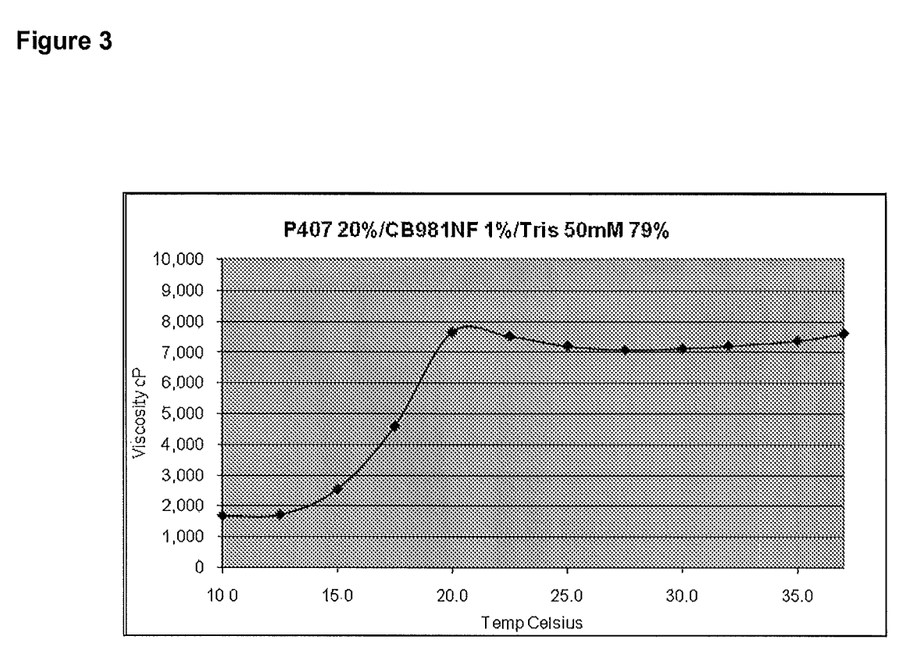
FIG. 3 depicts the dependence of viscosity (cP) on temperature (° C.) of a solution of poloxamer 407 (BASF Pluronic® F127) (20% w/w) and Carbopol 981NF (Lubrizol®) (1% w/w) in a 50 mM tromethamine solution in purified water. The viscosity was recorded using a Brookfield DV-II+ Pro viscometer at 50 rpm.

Poloxamer 407 (BASF Pluronic® F127) and Carbopol 981NF (Lubrizol®) were added to a solution of tromethamine (50 mM in purified water, pH 7.3) to create a solution of 20% (w/w) P407, 1% Carbopol 981NF, and 79% tromethamine buffer. Viscosity was recorded over a temperature range of 10° C. to 37° C. using a Brookfield DV-II+ Pro viscometer set at 50 rpm. The resulting viscosity vs. temperature curve appears in FIG. 3. FIG. 3 displays the reverse-thermosensitive nature of the solution due to the inclusion of P407. The peak viscosity of 7,636 cP at 20° C. was 358% that of the viscosity at 10° C. This significant increase in viscosity, along with the increased bioadhesion due to the presence of carbopol, resulted in a less slippery surface for the ultrasound probe, thus reducing unwanted probe movement. Also significant was the point of peak viscosity. At 20° C., roughly room temperature, the gel has already reached its higher viscosity state, compared to the previous example in which the peak viscosity is reached only after the solution is warmed to 25° C.

Figure 4:
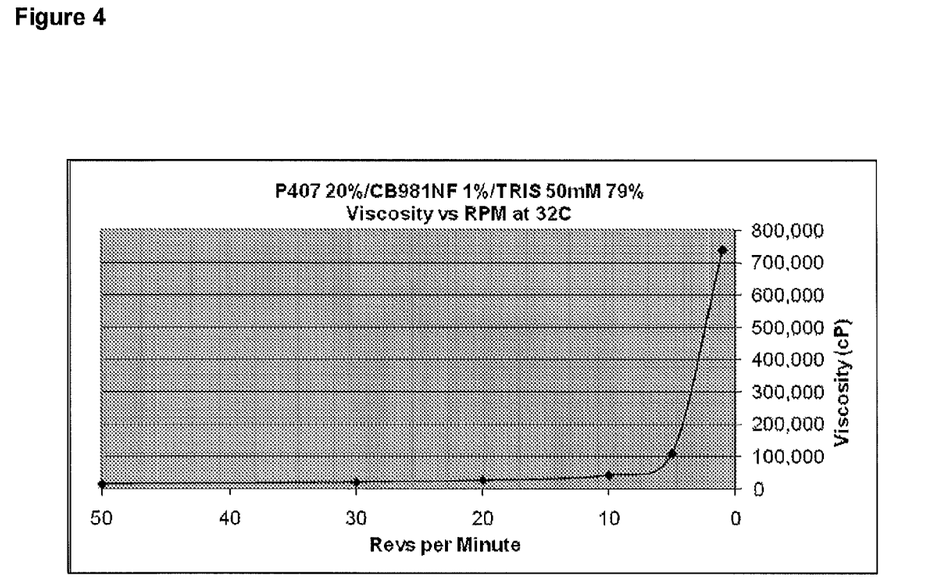
FIG. 4 depicts a rheological experiment illustrating the shear thinning nature of a solution of poloxamer 407 (BASF Pluronic® F127) (20% w/w) and Carbopol 981NF (Lubrizol®) (1% w/w) in a 50 mM tromethamine solution in purified water using the Brookfield viscometer ranging from 50 rpm to 0.5 rpm at 31° C.

Rheology was then performed using the Brookfield viscometer ranging from 50 rpm to 0.5 rpm at 31° C. The data are presented in FIG. 4. FIG. 4 displays the shear thinning nature of the solution. As the shear increased due to increasing rate of rotation of the viscometer, the viscosity decreased. This is significant in the ultrasound application. As the probe was brought to rest upon identifying the target location, the lack of shear stress on the gel yielded a more viscous gel. If the user initiated probe movement to fine-tune the probe location, the viscosity of the gel decreased, thus allowing easier movement of the probe.

EXAMPLE 3

Figure 5:
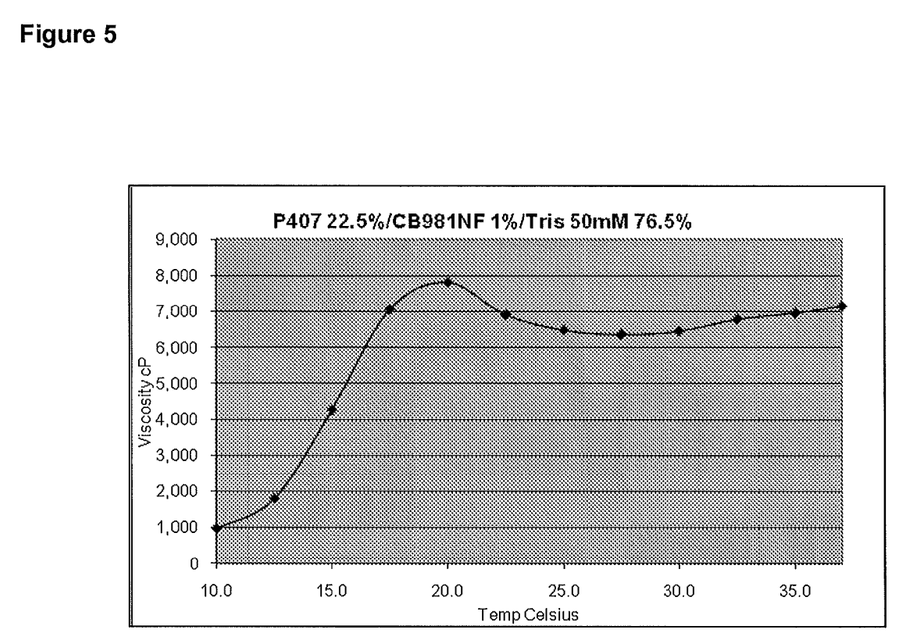
FIG. 5 depicts the dependence of viscosity (cP) on temperature (° C.) of a solution of poloxamer 407 (BASF Pluronic® F127) (22.5% w/w) and Carbopol 981NF (Lubrizol®) (1% w/w) in a 50 mM tromethamine solution in purified water. The viscosity was recorded using a Brookfield DV-II+ Pro viscometer at 50 rpm.

Poloxamer 407 (BASF Pluronic® F127) and Carbopol 981NF (Lubrizol®) were added to a solution of tromethamine (50 mM in purified water, pH 7.3) to create a solution of 22.5% (w/w) P407, 1% Carbopol 981NF, and 76.5% tromethamine buffer. Viscosity was recorded over a temperature range of 10° C. to 37° C. using a Brookfield DV-II+ Pro viscometer set at 50 rpm. The resulting viscosity vs. temperature curve is presented in FIG. 5. FIG. 5 displays the reverse-thermosensitive nature of the solution due to the inclusion of P407. The peak viscosity of 7,826 cP at 20° C. was 708% that of the viscosity at 10° C. This significant increase in viscosity, along with the increased bioadhesion due to the presence of carbopol, resulted in a less slippery surface for the ultrasound probe, thus reducing unwanted probe movement. Also significant is the point of peak viscosity. At 20° C., roughly room temperature, the gel has already reached its higher viscosity state. This is contrasted with the first example, in which the peak viscosity is reached only after the solution is warmed to 25° C.

EXAMPLE 4

Figure 6:
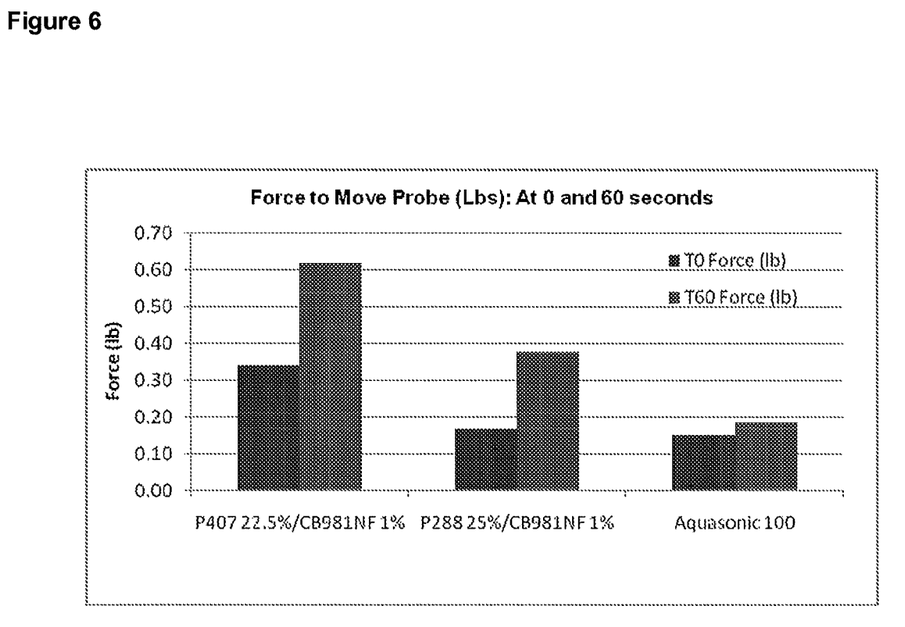
FIG. 6 depicts a comparison between three gels of the force required to move an object upon initial application and after 60 seconds. The data depicted on the left were gathered from experiments utilizing the following solution: poloxamer 407 (BASF Pluronic® F127) (22.5% w/w) and Carbopol 981NF (Lubrizol®) (1% w/w) in a 50 mM tromethamine solution in purified water. The data depicted in the middle were gathered from experiments utilizing the following solution: poloxamer 288 (BASF Pluronic® F98) (25% w/w) and Carbopol 981NF (Lubrizol®) (1% w/w), in a 50 mM tromethamine solution in purified water. The data depicted on the right were gathered from experiments utilizing commercially available Aquasonic® 100 (Parker Labs).

The force required to move a weighted plastic cylinder, upon initial application and then after 60 seconds, was compared for three different gels. Poloxamer 407 (BASF Pluronic® F127) and Carbopol 981NF (Lubrizol( ) were added to a solution of tromethamine (50 mM in purified water, pH 7.3) to create a solution of 22.5% (w/w) P407, 1% Carbopol 981NF and 76.5% tromethamine buffer solution for the first gel. The second gel comprised poloxamer 288 (BASF Pluronic® F98) and Carbopol 981 NF (Lubrizol®) in a solution of tromethamine (50 mM in purified water, pH 7.3). This created a solution of 25% (w/w) P288, 1% carbopol 981NF, and 74% tromethamine buffer solution. Aquasonic® 100 (Parker Labs) was purchased and was the third gel tested. A 5.5-cm diameter plastic cylinder was loaded to achieve a total weight of 117.5 grams. Four milliliters of each sample were applied to the skin and the loaded cylinder was placed on the gel. A scale (American Weigh Scales H11) with the ability to measure forces from 0.005 lbs to 11 lbs was used to measure the maximum force required to move the cylinder over a length of 2 inches. This was performed upon initial application of the gel to the skin and again after 60 seconds, a sufficient amount of time for the gel to warm to skin temperature. Twelve pairs of measurements (T=0 and T=60 seconds) were collected for P288 25%/CB981NF 1%/Tris 74%. Ten pairs of measurements (T=0 and T=60 seconds) were collected for P407 22.5%/CB981NF 1%/Tris 76.5%. Eight pairs of measurements (T=0 and T=60 seconds) were collected for Aquasonic 100. The average force required to move the cylinder for each gel is seen in FIG. 6.

The average force at T0 required to move the cylinder through the P407 22.5%/CB981NF 1% gel is 0.34 lbs. At T60, the force is 0.62 lbs, 81% higher. The average force at T0 required to move the cylinder through the P288 25%/CB981 NF 1% gel is 0.17 lbs. At T60, the force is 0.38 lbs, 128% higher. The average force at T0 required to move the cylinder through the Aquasonic 100 gel is 0.15 lbs. At T60, the force is 0.19 lbs, 22% higher. P288 25%/CB981NF 1% yielded an initial force sufficiently comparable to Aquasonic, and yet the force required increased substantially upon warming, thus aiding in the reduction of unwanted probe movement.

EXAMPLE 5

Figure 7:
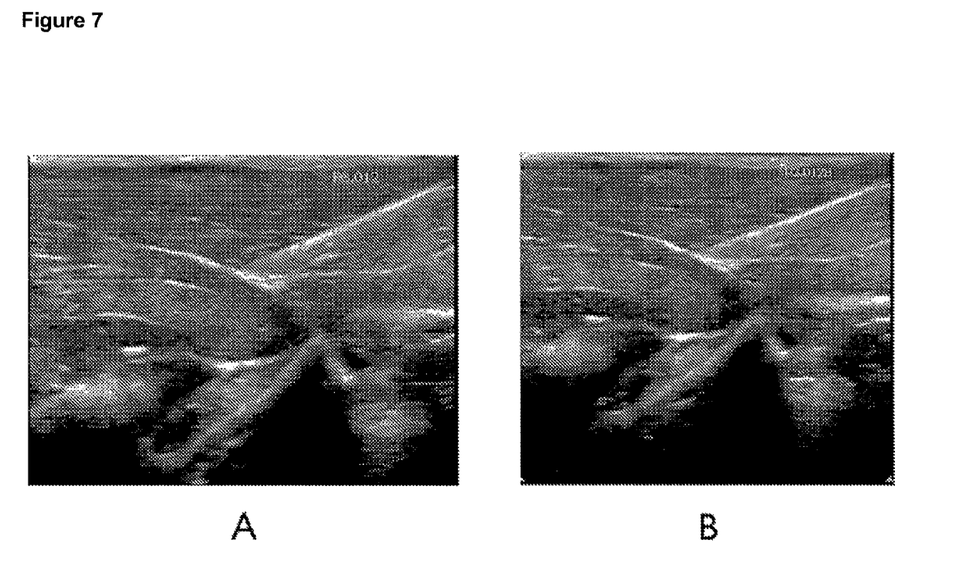
FIG. 7 depicts a representative pair of images visualized with Philips HD11XE at 12 MHz. The image in A was visualized using Aquasonic® 100; the image in B was visualized using Pluromed P288/CB981 gel.
Figure 8:
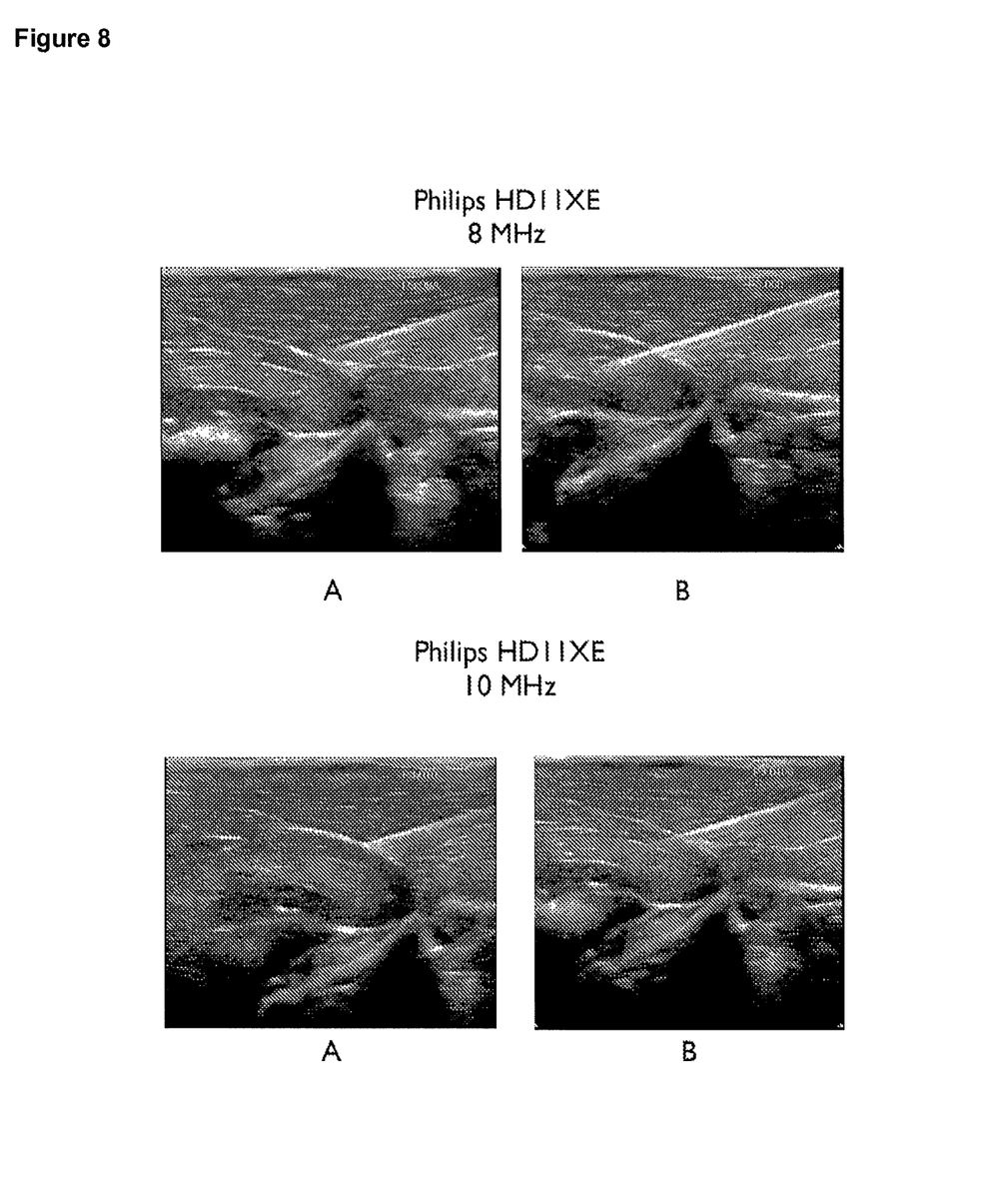
FIG. 8 depicts a pair of images visualized with Philips HD11XE at 8 MHz (top) and a pair of images visualized with Philips HD11XE at 10 MHz (bottom). In both cases, the image in A was visualized using Aquasonic® 100; the image in B was visualized using Pluromed P288/CB981 gel.
Figure 9:
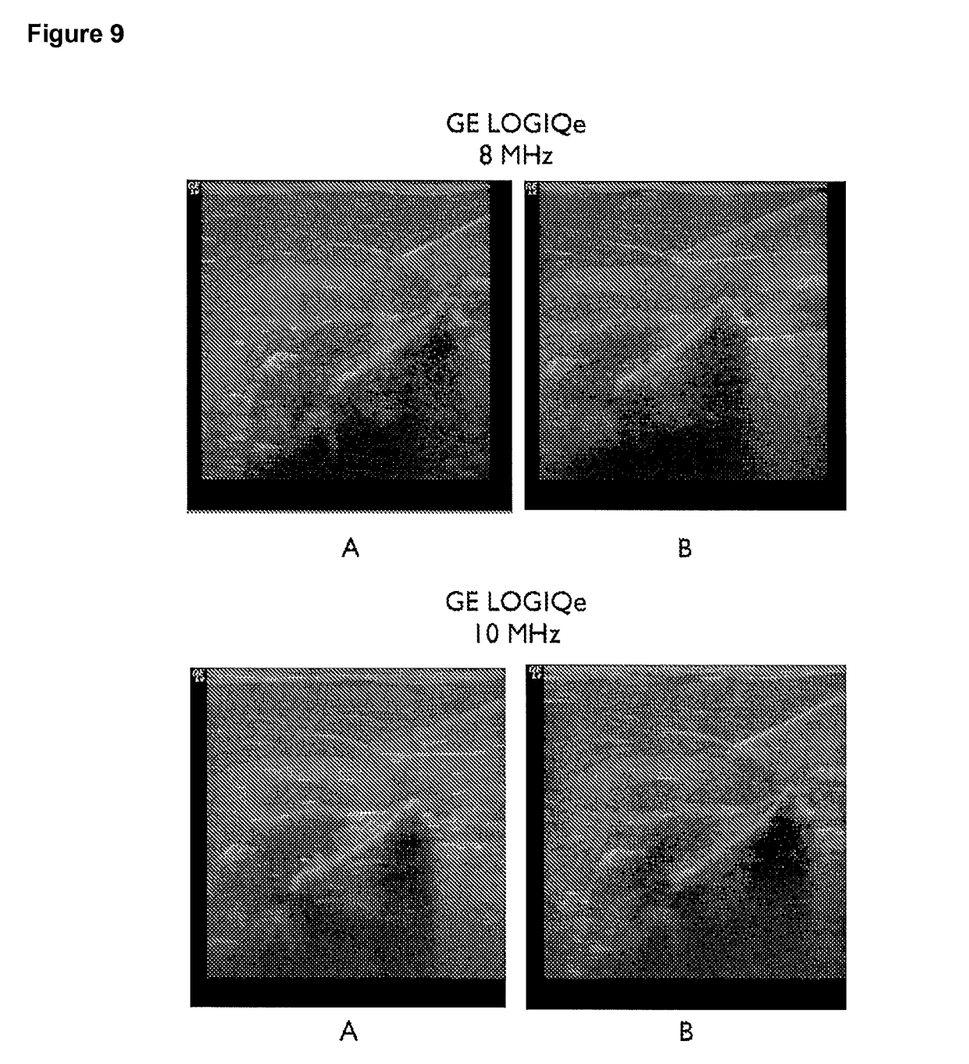
FIG. 9 depicts a pair of images visualized with GE LOGIQe at 8 MHz (top) and a pair of images visualized with GE LOGIQe at 10 MHz (bottom). In both cases, the image in A was visualized using Aquasonic® 100; the image in B was visualized using Pluromed P288/CB981 gel.
Figure 10:
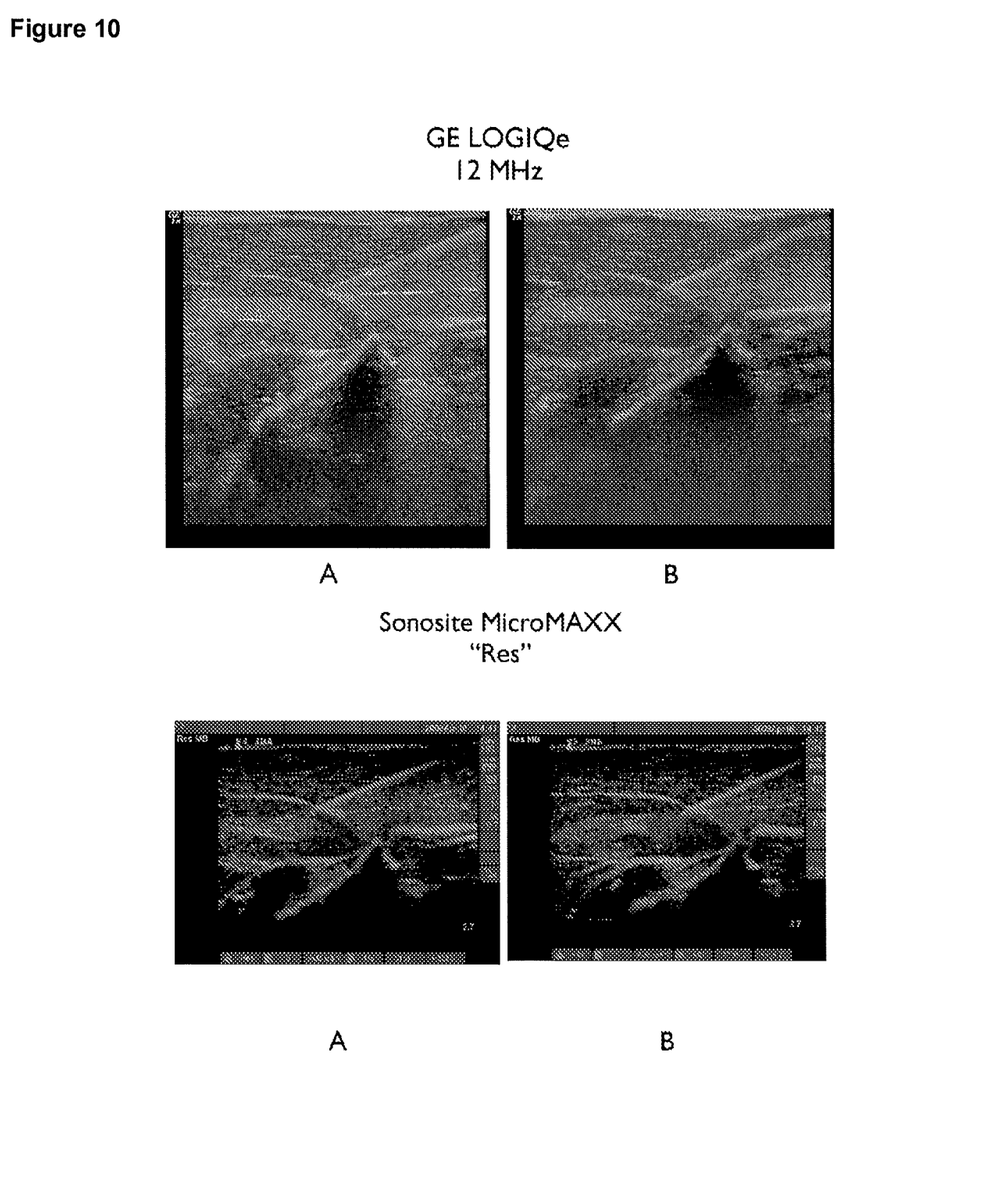
FIG. 10 depicts a pair of images visualized with GE LOGIQe at 12 MHz (top) and a pair of images visualized with Sonosite MicroMAXX using the "Res" setting (bottom). In both cases, the image in A was visualized using Aquasonic® 100; the image in B was visualized using Pluromed P288/CB981 gel.
Figure 11:
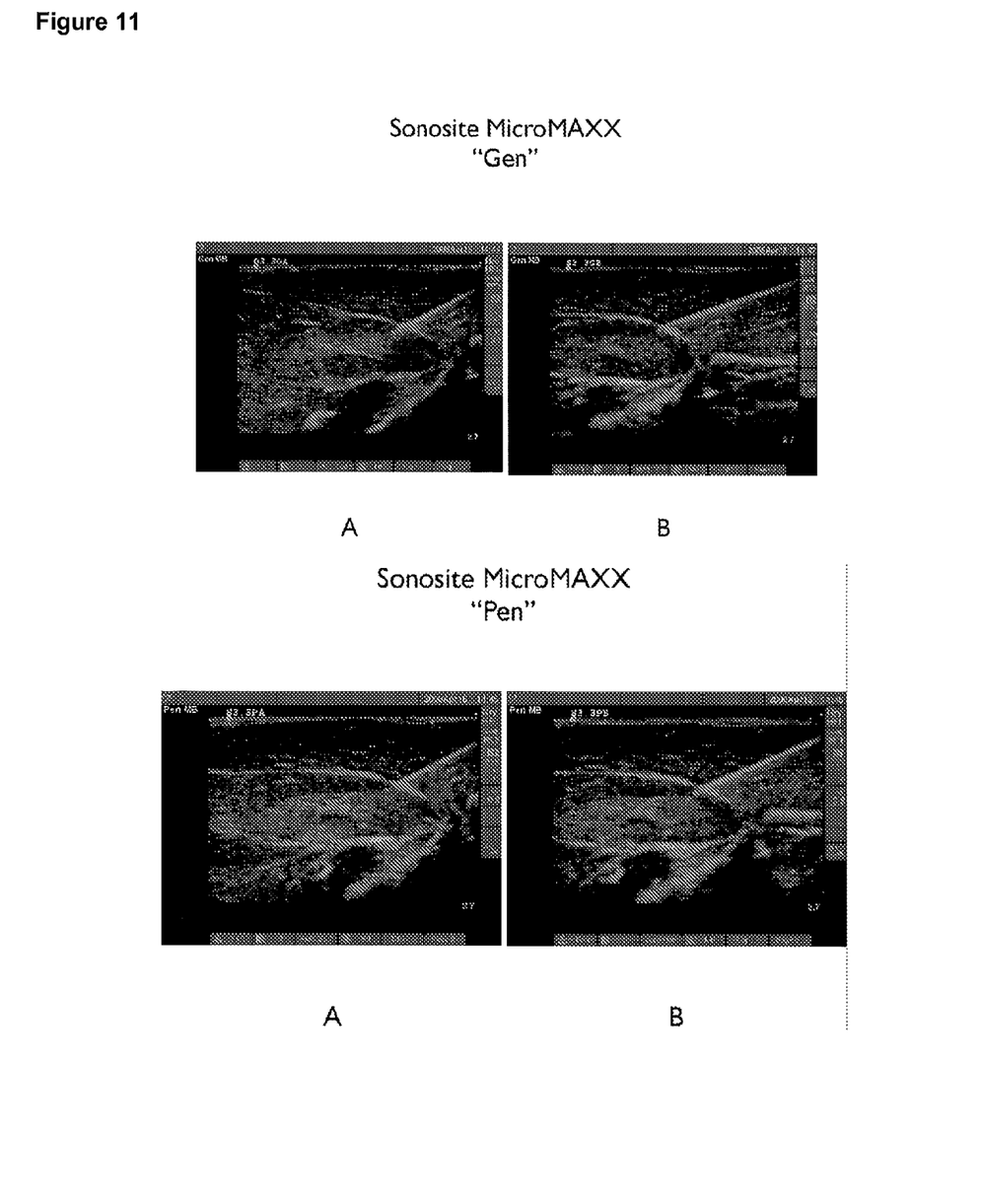
FIG. 11 depicts a pair of images visualized with Sonosite MicroMAXX using the "Gen" setting (top) and a pair of images visualized with Sonosite MicroMAXX using the "Pen" setting (bottom). In both cases, the image in A was visualized using Aquasonic® 100; the image in B was visualized using Pluromed P288/CB981 gel.
Figure 12:
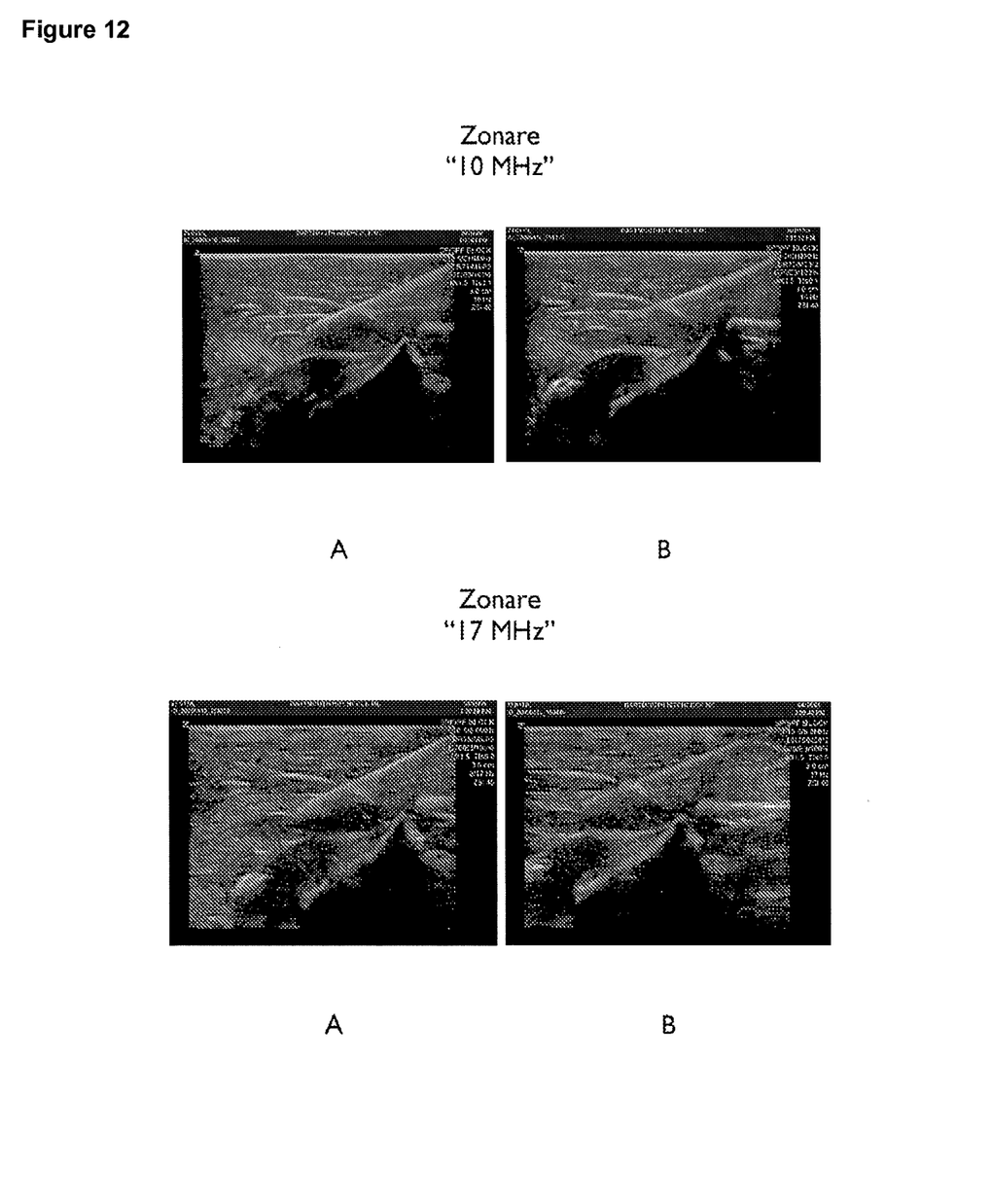
FIG. 12 depicts a pair of images visualized with Zonare at 10 MHz (top) and a pair of images visualized with Zonare at 17 MHz (bottom). In both cases, the image in A was visualized using Aquasonic® 100; the image in B was visualized using Pluromed P288/CB981 gel.

Two gels were compared in their ability to transmit ultrasound waves. An ex vivo model was designed to simulate an ultrasound-guided peripheral nerve block procedure, in which a needle is inserted towards a target under ultrasound visualization. A turkey breast was used as a phantom. Poloxamer 288 (BASF Pluronic® F98) and Carbopol 981NF (Lubrizol®) were added to a solution of tromethamine (50 mM in purified water, pH 7.3) to create a solution of 25% (w/w) P288, 1% Carbopol 981NF, and 74% tromethamine buffer solution. Commercially available Aquasonic® 100 (Parker Labs) was purchased. Four different ultrasound systems were used with different frequency settings. The 11 ultrasound system/frequency setting iterations evaluated were:

Sonosite MicroMAXX—L38 probe
  'Res'
  'Gen'
  'Pen'
Zonare—L10-5 probe
  10 MHz
  17 MHz
GE LOGIQe—12L probe
  8 MHz
  10 MHz
  12 MHz
Philips HD11XE—L12-3 probe
  8 MHz
  10 MHz
  12 MHz The P288/CB981 gel was allowed to come to temperature in a 37° C. water bath before being applied to the turkey breast. An image was captured by an experienced anesthesiologist for both gels for each of the 11 ultrasound system/frequency setting iterations. The images (depicted in FIGS. 7-12) were then evaluated by 10 blinded evaluators who rated the image quality for each pair as follows:

a. Sample A is a better image
b. Sample B is a better image
c. There is no clinical difference between images A and B A representative image pair is the Philips HD11XE at 12 MHz (FIG. 7). The images are clinically indistinguishable. In both images, a block needle is clearly visualized entering the tissue from the upper right corner of the image. Muscle appears the same in both images with very good resolution of fine internal structure, while a brightly echogenic fascial plane is crisply defined in both images. Deeper bony and fascial structures are equally visualized in both images. Any very slight differences in the images can be attributed to subtle differences in probe position relative to the specimen.

The results of the comparisons by the 10 blinded evaluators are seen below in Table 1. If Sample A (Aquasonic 100) was preferred, a score of −1 is entered. If Sample B (P288 25%/CB981NF 1%) was preferred, a score of +1 is entered. If no clinical difference was found, a score of 0 is entered. Eight out of 10 reviewers indicated that, over the spectrum of all samples, Sample B (P288 25%/CB981NF 1%) provided a preferred image. Two out of ten reviewers indicated that, over the spectrum of all samples, there was no clinical difference between the two samples. Of the 110 total sample pair evaluations, Sample A (Aquasonic 100) was preferred 25.5% of the time, Sample B (P288 25%/CB981NF 1%) was preferred 42.7% of the time, and no clinical difference was found 31.8% of the time.

TABLE 1

| System/Frequency | Rev 1 | Rev 2 | Rev 3 | Rev 4 | Rev 5 | Rev 6 | Rev 7 | Rev 8 | Rev 9 | Rev 10 | Avg by sample |
|---|---|---|---|---|---|---|---|---|---|---|---|
| Philips HD11XE - 8 MHz | 0 | 1 | −1 | 1 | 1 | 1 | 1 | 0 | −1 | 1 | 0.40 |
| Philips HD11XE - 10 MHz | 1 | 1 | 1 | 1 | 1 | 1 | 1 | 0 | 1 | 1 | 0.90 |
| Philips HD11XE - 12 MHz | 1 | 0 | 0 | 0 | 1 | −1 | 0 | 0 | 0 | 0 | 0.10 |
| GE LOGIQe - 8 MHz | 1 | −1 | 0 | 0 | 1 | 1 | 1 | 1 | −1 | −1 | 0.20 |
| GE LOGIQe - 10 MHz | −1 | 1 | −1 | 1 | −1 | 1 | 0 | 1 | 1 | 1 | 0.30 |
| GE LOGIQe - 12 MHz | −1 | −1 | −1 | 0 | −1 | −1 | 0 | 0 | −1 | 1 | −0.50 |
| Sonosite MicroMAXX - Res | 1 | 1 | 0 | 0 | 1 | 0 | 0 | 0 | 1 | 0 | 0.40 |
| Sonosite MicroMAXX - Gen | 1 | 1 | 1 | 0 | 0 | 1 | 1 | 1 | 1 | 0 | 0.70 |
| Sonosite MicroMAXX - Pen | 1 | −1 | 1 | 0 | 0 | 1 | 0 | 0 | 1 | 1 | 0.40 |
| Zonare - 10 MHz | −1 | −1 | 0 | 0 | −1 | 1 | −1 | −1 | −1 | 0 | −0.50 |
| Zonare - 17 MHz | 1 | −1 | 0 | 0 | −1 | −1 | −1 | −1 | 0 | −1 | −0.50 |
| Average by Reviewer | 0.36 | 0.00 | 0.00 | 0.27 | 0.09 | 0.36 | 0.18 | 0.09 | 0.09 | 0.27 | |
| Average of Total | 0.17 | | | | | | | | | | |

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method of ultrasonography, comprising the steps of: applying a gel to a surface to give a gel-coated surface; and contacting the gel-coated surface with an ultrasound probe; wherein the gel consists essentially of 10% to about 50% (wt/wt) of the reverse phase polymer selected from the group consisting of poloxamer 407, poloxamer 188, poloxamer 288, and poloxamer 338, and high molecular weight polyacrylic acid additive in concentration of about 0.1% to about 3% (wt/wt) to increase the adhesiveness of the gel and wherein the surface is patient's skin.

2. The method of claim 1, wherein the reverse phase polymer has been purified.

3. The method of claim 1, wherein the gel comprises about 20% to about 40% (wt/wt) of the reverse phase polymer.

4. The method of claim 1, wherein the pH of the gel is about 3.0 to about 8.0.

5. The method of claim 1, wherein the gel further comprises a dye, hormone, therapeutic agent, filler, antiseptic, preservative, or antimicrobial agent.

6. The method of claim 1, wherein the additive is a polyacrylic acid cross-linked with a polyalkenyl ether, or polyacrylic acid cross-linked with divinyl glycol.

7. The method of claim 6, wherein the concentration of additive in the gel is about 0.1% to about 3% (wt/wt).

8. The method of claim 7, wherein the additive is polycarbophil, sodium alginate, sodium chloride, sodium dihydrogen phosphate, sodium monohydrogen phosphate, protamine, or a polysaccharide.

9. The method of claim 1, wherein the additive is polycarbophil, sodium alginate, sodium chloride, sodium dihydrogen phosphate, sodium monohydrogen phosphate, protamine, or a polysaccharide.

10. The method of claim 1, wherein the additive is a compound that does not eliminate the reverse phase thermosensitive properties of the gel.

11. The method of claim 1, wherein the concentration of additive in the gel is about 0.5% to about 2% (wt/wt).

12. A method of ultrasonography, comprising the steps of: applying a gel to a surface to give a gel-coated surface; and contacting the gel-coated surface with an ultrasound probe; wherein the gel consists essentially of 10% to about 50% (wt/wt) of poloxamer 407 or poloxamer 288 and an additive to increase the adhesiveness of the gel wherein the concentration of additive in the gel is about 0.1% to about 3% (wt/wt) and wherein the surface is patient's skin.

13. The method of claim 12, wherein the additive is a polyacrylic acid cross-linked with a polyalkenyl ether, or polyacrylic acid cross-linked with divinyl glycol.

14. The method of claim 12, wherein the additive is polycarbophil, sodium alginate, sodium chloride, sodium dihydrogen phosphate, sodium monohydrogen phosphate, protamine, or a polysaccharide.

* * * * *